United States Patent [19]
Resnick et al.

[11] Patent Number: 5,651,790
[45] Date of Patent: Jul. 29, 1997

[54] METHOD AND APPARATUS FOR SUBLIGAMENTOUS ENDOSCOPIC TRANSVERSE CARPAL LIGAMENT RELEASE SURGERY

[75] Inventors: Charles T. Resnick, La Canada; Brent W. Miller, Bradburg, both of Calif.

[73] Assignee: Milres Corporation, Los Angeles, Calif.

[21] Appl. No.: 444,435

[22] Filed: May 19, 1995

Related U.S. Application Data

[62] Division of Ser. No. 157,225, Nov. 22, 1993, which is a continuation of Ser. No. 763,086, Sep. 20, 1991, Pat. No. 5,282,816.

[51] Int. Cl.$^6$ .................................................. A61B 17/32
[52] U.S. Cl. .................................. 606/167; 606/170
[58] Field of Search ........................ 606/167, 170, 606/180, 181, 182, 185, 160, 108; 128/898, 772; 604/264, 280

[56] References Cited

U.S. PATENT DOCUMENTS

| | | | |
|---|---|---|---|
| 379,553 | 3/1888 | Allen | 600/184 |
| 1,880,551 | 10/1932 | Wappler | 600/104 |
| 2,256,942 | 9/1941 | Duffy | 604/164 |
| 2,676,595 | 4/1954 | Dyekjaer | 606/167 |
| 2,838,049 | 2/1958 | Eisenhofer et al. | 606/167 |
| 3,241,236 | 3/1966 | Capps | 30/287 |
| 3,256,874 | 6/1966 | DeMarco | 606/170 |
| 4,254,762 | 3/1981 | Yoon | 600/114 |
| 4,449,532 | 5/1984 | Storz | 606/191 |
| 4,497,320 | 2/1985 | Nicholson et al. | 606/170 |
| 4,610,242 | 9/1986 | Santangelo et al. | 600/114 |
| 4,620,527 | 11/1986 | Adams, Jr. | 600/102 |
| 4,656,999 | 4/1987 | Storz | 60/452 |
| 4,674,500 | 6/1987 | DeSatnick | 606/170 |
| 4,712,546 | 12/1987 | Noe | 606/170 |
| 4,723,546 | 2/1988 | Zagorski | 606/170 |
| 4,766,896 | 8/1988 | Pao | 606/170 |
| 4,790,312 | 12/1988 | Capuano et al. | 606/171 |
| 4,798,193 | 1/1989 | Giesy et al. | 600/114 |
| 4,819,620 | 4/1989 | Okutsu | 600/114 |
| 4,924,882 | 5/1990 | Donovan | 128/898 |
| 4,962,770 | 10/1990 | Agee et al. | 128/898 |
| 4,985,035 | 1/1991 | Torre | 606/167 |
| 5,029,573 | 7/1991 | Chow | 128/4 |
| 5,071,408 | 12/1991 | Ahmed | 606/108 |
| 5,127,419 | 7/1992 | Kaldany | 606/170 |
| 5,253,659 | 10/1993 | McNamara et al. | 128/898 |
| 5,269,290 | 12/1993 | Barrett et al. | 600/101 |
| 5,269,796 | 12/1993 | Miller et al. | 606/167 |
| 5,273,024 | 12/1993 | Menon et al. | 600/114 |
| 5,275,611 | 1/1994 | Behl | 604/264 |
| 5,323,765 | 6/1994 | Brown | 600/104 |

FOREIGN PATENT DOCUMENTS

| | | | |
|---|---|---|---|
| 3139480 A1 | 4/1983 | Germany . | |
| 3624243 A1 | 1/1988 | Germany . | |
| 0133553 | 1/1960 | U.S.S.R. | 606/167 |
| 1011-120-A | 4/1983 | U.S.S.R. | 606/167 |
| WO90/02524 | 9/1989 | WIPO . | |

OTHER PUBLICATIONS

Paul L. Cusick, "Cyclodialysis with Goniotomy in Congenital Glaucoma" Am. Jour. Ophth., vol. 38, No. 5, Nov. 1954, pp. 712–714.

International Search Report, PCT/US92/07989, Jan. 1993.

Neuro Surgical Catalog—1986—Codman & Shurtliff, Inc.

(List continued on next page.)

*Primary Examiner*—Edgar S. Burr
*Assistant Examiner*—Anthony H. Nguyen
*Attorney, Agent, or Firm*—LaRiviere, Grubman & Payne

[57] ABSTRACT

A cannula for use in endoscopic surgical procedures, the procedures including use of an endoscope and a surgical instrument. The cannula has two ends with a continuous passageway extending between the ends. The cannula has a slot extending along its length through which tissue can be viewed by the endoscope and accessed by the surgical instrument. The slot is bounded by a crosspiece at one of its ends. The cannula may be tapered and may have a guard at the end of the cannula opposite the crosspiece.

4 Claims, 7 Drawing Sheets

OTHER PUBLICATIONS

Jarit Surgical Instrument Catalog—Copyright 1987, J. Jamner Surgical Instruments, Inc.

Storz Surgical Instruments—Copyright 1989—Storz Instrument Company.

Arthroscopy Catalog—1984 Edition—Karl Storz GmbH & Co. Manufacturer of Endoscopes.

Amis et al. "Painful Heel Syndrome: Radiographic and Treatment Assessment", Foot & Ankle, vol. 9, No. 2, Oct. 1988, pp. 91–95.

Anderson et al. "Operative Treatment of Subcalcaneal Pain", Foot Fellows Review, Foot & Ankle, vol. 9, No. 6, Jun. 1989, pp. 317–323.

Baerg "Calcaneal Decompression for Heel Pain", Clinics in Podiatric Medicine and Surgery, vol. 8, No. 1, Jan. 1991, pp. 197–202.

Barrett et al. "Endoscopic Plantar Fasciotomy for Chronic Plantar Fasciitis/Heel Spur Syndrome: Surgical Technique—Early Clinical Results", The Journal of Foot Surgery, vol. 30, No. 6, 1991, pp. 568–570.

Baxter et al. "Heel Pain—Operative Results", Foot & Ankle, vol. 5, No. 1, 1984, pp. 16–25.

Beaver "The Surgeon's Choice in Quality Blades and Knife Systems", Catalog, Becton Dickinson and Company, 1990.

Beito et al. "Recalcitrant Heel Pain—Traumatic Fibrosis versus Heel Neuroma", Journal of the American Podiatric Medical Association, vol. 79, No. 7, Jul. 1989, pp. 336–339.

Berkowitz et al. "Plantar Fasciitis: MR Imaging", Radiology, 1991.

Dailey "Differential Diagnosis and Treatment of Heel Pain", Clinics in Podiatric Medicine and Surgery, vol. 8, No. 1, Jan. 1991, pp. 187–195.

Golding "Treatable Causes of a Painful Heel", Correspondence, Hill and Cutting, Heel Pain & Body Weight, Foot & Ankle, 1989.

Goulet "Role of Soft Orthosis in Treating Plantar Fasciitis—Suggestion from the Field", Physical Therapy, p. 1544.

Hepford "Minimal Incision Surgical Approach to Mechanical Heel Pain", Clinics in Podiatric Medicine and Surgery, vol. 8, No. 1, Jan. 1991, pp. 167–185.

Hill, Jr. et al. "Heel Pain and Body Weight", Foot & Ankle, vol. 9, No. 5, Apr. 1989, pp. 254–256.

Hoffman et al. "Fractures of the Calcaneus Secondary to Heel Spur Surgery—Analysis and Case Report", Journal of the American Podiatric Medical Association, vol. 75, No. 5, May 1985, pp. 267–271.

Intenzo, et al. "Evaluation of Plantar Fasciitis by Three–phase Bone Scintigraphy", Clinical Nuclear Medicine, vol. 16, No. 5, May 1991, pp. 325–328.

Jacoby et al. "Surgical Management of Recalcitrant Heel Pain", Clinics in Podiatric Medicine and Surgery, vol. 8, No. 1, Jan. 1991, pp. 187–195.

Jay et al. "Calcaneal Decompression for Chronic Heel Pain", Journal of the American Podiatric Medical Association, vol. 75, No. 10, Oct. 1985, pp. 535–537 (Letters to the Editor, vol. 76, No. 6, Jun. 1986, pp. 364–365.).

Kenzora "The Painful Heel Syndrome: An Entrapment Neuropathy", Bulletin of the Hospital for Joint Diseases Orthopaedic Institute, vol. 47, No. 2, 1987, pp. 178–189.

Lapidus et al. "Painful Heel: Report of 323 Patients With 364 Painful Heels", pp. 178–186.

Leach et al. "Results of Surgery in Athletes with Plantar Fasciitis", Foot & Ankle, vol. 7, No. 3, Dec. 1986, pp. 156–161.

LeMelle et al. "Chronic Plantar Fascial Inflammation and Fibrosis", Clinics in Podiatric Medicine and Surgery, vol. 7, No. 2, Apr. 1990, pp. 385–389.

Lester, et al. "Surgical Treatment of Plantar Fasciitis", Clinical Orthopaedics and Related Research, No. 186, Jun. 1984, pp. 202–204.

Lutter "Surgical Decisions in Athletes' Subcalcaneal Pain", The American Journal of Sports Medicine, vol. 14, No. 6, 1986, pp. 481–485.

Mallay "Heel Surgery", Section 3: Fundamental Conditions and Procedures, Chapter 16: Heel Surgery, pp. 431–440.

Meltzer "A Rational Approach to the Management of Heel Pain—A Protocol Proposal", Journal of the American Podiatric Medical Association, vol. 79, No. 2, Feb. 1989, pp. 89–92.

Mueller "The Surgical Armamentarium" Baxter Operating Room Division Catalog, 1988.

O'Brien et al. "A Retrospective Analysis of Heel Pain", Journal of the American Podiatric Medical Association, vol. 75, No. 8, Aug. 1985, pp. 416–418.

Onuba et al. "Plantar Fasciitis", Italian Journal of Orthopaedics and Traumatology, vol. 12, No. 4, Dec. 1986, pp. 533–535.

Polisner "Early Ambulation After Minimal Incision Surgery for Calcaneal Spurs", Clinics in Podiatry, vol. 2, No. 3, Jul. 1985, pp. 497–502.

Richard Wolf Medical Instruments Corp., "Panoview™ Telescopes".

Schwartz "Inferior Heel Spur Surgery", Clinics in Podiatric Medicine and Surgery, vol. 7, No. 2, Apr. 1990, pp. 261–270.

Sebes "The Significance of Calcaneal Spurs in Rheumatic Diseases", Arthritis and Rheumatism, vol. 32, No. 3, Mar. 1989, pp. 338–440.

Shmokler et al. "A New Use of Instrumentation in Fluoroscopy Controlled Heel Spur Surgery", Journal of the American Podiatric Medical Association, vol. 78, No. 4, Apr. 1988, pp. 194–197.

Snider et al. "Plantar Fascia Release for Chronic Plantar Fasciitis in Runners", The American Journal of Sports Medicine, vol. 11, No. 4, 1983, pp. 215–219.

Turlik "Seronegative Arthritis as a Cause of Heel Pain", Clinics in Podiatric Medicine and Surgery, vol. 7, No. 2, Apr. 1990, pp. 369–375.

Ward et al. "Proximal Medial Longitudinal Arch Incision for Plantar Fascia Release", Foot & Ankle, vol. 8, No. 3, Dec. 1987, pp. 152–155.

METHOD AND APPARATUS FOR SUBLIGAMENTOUS ENDOSCOPIC TRANSVERSE CARPAL LIGAMENT RELEASE SURGERY

The application is a divisional of application Ser. No. 08/157,225, filed Nov. 22, 1993, which is a continuation of application Ser. No. 07/763,086, filed Sep. 20, 1991, now U.S. Pat. No. 5,282,816.

TECHNICAL FIELD

This invention relates to an endoscopic surgical technique for releasing the transverse carpal ligament and more particularly to a method in which access to the carpal tunnel is gained without retracting the flexor tendons or ulnar neurovascular structures and in which special angled instruments are used for releasing the carpal ligament.

BACKGROUND ART

I. Okutsu et al., in an article entitled Endoscopic Management of Carpal Tunnel Syndrome, *Arthroscopy*, 5(1):11–18 (1989), describe a subcutaneous endoscopic procedure for releasing the transverse carpal ligament that utilizes an endoscope inserted in a clear plastic tube to view the ligament, and a hooked retrograde knife to release the ligament. Okutsu et al. also describe the use of an L-shaped probe to clear the synovial membrane from the transverse carpal ligament in order to facilitate viewing of the ligament.

Simultaneously with the report by Okutsu et al., James C. Y. Chow, M.D., in an article entitled Endoscopic Release of the Carpal Ligament: A New Technique for Carpal Tunnel Syndrome, *Arthroscopy*, 5(1):19–24 (1989), reported an endoscopic technique for releasing the transverse carpal ligament using a hooked knife inserted in a slotted arthroscopy sheath. A follow-up article by Dr. Chow, entitled Endoscopic Release of the Carpal Ligament for Carpal Tunnel Syndrome: 22-Month Clinical Result, *Arthroscopy*, 6(4):288–296 (1990), further describes the technique. A product brochure entitled A Breakthrough in Carpal Tunnel Release, published by Smith & Nephew Dyonics, Inc. of Andover, Mass. in 1990, illustrates the surgical instruments used in performing the technique described in Dr. Chow's journal articles. A second brochure entitled An Illustrated Guide to Endoscopic Release of the Carpal Ligament, published by Smith & Nephew Dyonics, Inc. of Andover, Mass. in 1991, describes the technique in further detail and illustrates the instruments used in the procedure.

In Dr. Chow's technique, after access to the flexor canal is gained by incising the volar antebrachial fascia, the flexor tendons are retracted toward the radial side using a pair of blunt retractors. This provides a space into which the slotted cannula/obturator assembly is inserted. It is believed that this retraction of the flexor tendons places undue traction upon both the ulnar and media neurovascular structures and results in an increased incidence of postoperative media and ulnar nerve neurapraxiae. In addition, the ulnar neurovascular structures are placed at risk by unnecessarily deep dissection into the carpal canal.

Another problem with Dr. Chow's technique is that the proximity of the slotted cannula to the patient's fingers and forearm makes it awkward for the surgeon to manipulate the surgical tools in the cannula during the surgery. Additionally, Dr. Chow's technique employs a five-step cutting process to release the transverse carpal ligament, a process that complicates and prolongs the surgical procedure.

A preliminary report suggesting a simplified procedure for overcoming these problems was made by Drs. Charles T. Resnick and Brent W. Miller in an article entitled Endoscopic Carpal Tunnel Release Using the Subligamentous Two-portal Technique, *Contemporary Orthopaedics*, 22:3, 269–277 (1991).

DISCLOSURE OF INVENTION

According to the present invention, an improved technique for releasing the transverse carpal ligament employs a subligamentous approach to accessing the carpal tunnel and utilizes specially designed surgical tools to increase the surgeon's maneuverability and comfort.

The specially designed surgical tools comprise a midsection that is connected to a handle bent at an approximately 21 degree angle to the longitudinal axis of the midsection. By positioning the handle at an angle to the working end, the surgeon is able to hold the instrument comfortably without bumping into the patient's forearm or hand, and particularly the patient's fingers, while performing the release of the carpal ligament, thereby increasing the speed with which the surgery is performed.

The specific design of the working end varies depending on the function of the instrument. For example, the working end can be a knife blade (several possible designs), a blunt probe, a rasp or a curette. Specific working ends are described herein that are optimized for performing the transverse carpal ligament release using the subligamentous technique.

In the subligamentous technique of the present invention, an entrance portal is established substantially as is done in the Chow technique. However, after the volar antebrachial fascia is incised to expose the flexor tendons, neither the flexor tendons nor the ulnar nerve are retracted. Rather, a cannula/obturator assembly is placed under the flexor retinaculum using direct visualization and the cannula/obturator assembly is then moved into position by using gentle pressure to "walk" the assembly under the transverse carpal ligament. The exit portal is carefully identified in the palm of the hand, a horizontal incision is made and the assembly is pushed through the subcutaneous tissue and skin, thereby positioning the cannula/obturator assembly in the desired location for the release of the transverse carpal ligament. At this point, the cannula/obturator is in approximately the same position as it would have been in had the Chow technique been used. It also avoids inadvertent entrapment of the little finger sublimis tendon, avoiding potential iatrogenic laceration. However, it is felt that the subligamentous approach to positioning the cannula/obturator assembly in the carpal tunnel is less likely to damage the ulnar neurovascular structures or median nerve because it avoids the dissection to the floor of the flexor canal utilized in the Chow technique and also may be more superficial to the tenosynovium, thus increasing visualization of the undersurface of the transverse carpal ligament.

The obturator is then withdrawn from the cannula and an endoscope is placed in the proximal port of the cannula. Visualization of the transverse carpal ligament through the slot in the cannula is established. The specially designed rasp or curette of the present invention is inserted in the distal portal of the cannula and is used to clear away tissue such as the remaining ulnar bursa/tenosynovium that interferes with visualization of the transverse carpal ligament.

When visualization of the carpal ligament is unobstructed, the rasp or curette is withdrawn from the cannula and replaced with the specially designed puncture knife of the present invention. The puncture knife is used to make a hole in the distal third of the transverse carpal ligament. The puncture knife is then replaced with the specially designed reverse cut knife of the present invention. The reverse cut knife is inserted into the hole in the carpal ligament and the ligament is cut in a retrograde direction (proximal to distal), thereby releasing the distal half of the carpal ligament.

The reverse cut knife is removed from the cannula, the endoscope is moved to the distal end of the cannula and the reverse cut knife is inserted into the proximal end of the cannula, the cut in the ligament is located and the reverse cut knife is used to complete the release of the carpal ligament by cutting in a second direction (distally to proximally). Therefore, according to the method of the present invention, the release of the carpal ligament is achieved using three knife (cutting) steps as opposed to the five steps utilized in the Chow technique. The reduced number of cutting steps speeds up the operation, decreases the amount of time the instruments are inside the patients carpal tunnel and decreases the trauma, such as swelling, to the patient.

BRIEF DESCRIPTION OF DRAWINGS

For fuller understanding of the present invention, reference is made to the accompanying drawing in the following detailed Description of the Preferred Embodiment of the invention. In the drawing.

Reference numbers refer to the same or equivalent parts of the present invention throughout the several figures of the drawing.

BEST MODE OF CARRYING OUT THE INVENTION

Figure 1:
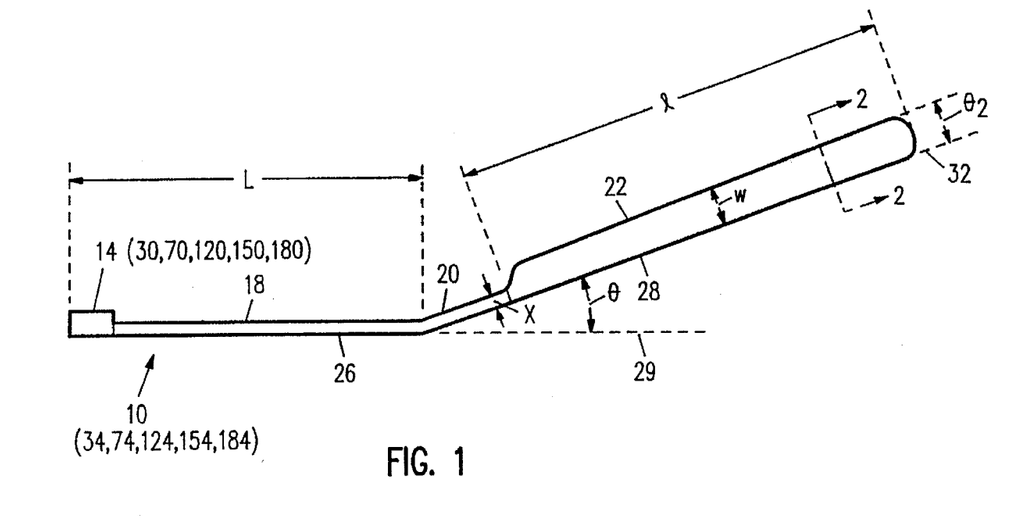
FIG. 1 is a side view of an angled surgical tool according to the present invention.

FIG. 1 illustrates the preferred embodiment of an angled surgical tool 10 for use in an endoscopic surgical procedure on a human hand, such as the release of the transverse carpal ligament. The angled surgical tool 10 comprises a working end 14, a midsection 18, a connecting section 20 and a handle 22. Although the tool 10 is described as comprising four parts, it should be appreciated that these are descriptive labels and do not imply that the tool 10 is necessarily constructed of four separate physical parts. In fact, in the preferred embodiment, the tool 10 is constructed from a single continuous piece of metal, and the terms working end 14, midsection 18, connecting section 20 and handle 22 merely refer to different sections of the same continuous piece of metal, such as stainless steel 440C cutlery supply (hot rolled annealed) with a heat-treated finish (Rc 50–54).

The handle 22 is the part of the tool 10 that is gripped by the surgeon while the tool 10 is being used. The handle 22 has a representative width "w" and is positioned at an angle θ. The angle θ is measured relative to a bottom edge 26 of the midsection 18 and a bottom edge 28 of the handle 22. Stated more generally, the angle θ is defined by a first line 29 that runs parallel to the direction of the midsection 18 and a second line 32 that runs parallel to the direction of the handle 22.

The handle 22 is connected to the midsection 18 by the connecting section 20. The connecting section 20 has a width "x" which is substantially narrower than the representative width w of the handle 22, thereby providing a region that is easier to bend than the handle 22 for establishing the angle θ. The connecting section 20 abuts the handle 22 and the midsection 18 thereby connecting these two sections. The connecting section 20 includes a bend that occurs at the interface of the connecting section 20 and the midsection 18 thereby forming the angle θ that exists between the midsection 18 and the handle 22. The angle θ may be measured between the longitudinal axes of midsection 18 and handle 22.

Since the connecting section 20 generally includes a bottom edge that is collinear and/or parallel to the bottom edge 28, the angle θ also exists between the connecting section 20 and the midsection 18.

Figure 2:
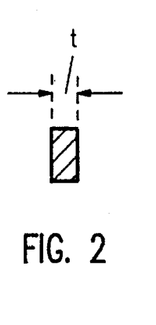
FIG. 2 is a cross-sectional view of the angled surgical tool taken along the line 2—2 shown in FIG. 1.

The term representative width, w, means the approximate average width of the handle 22 taking into consideration the fact that the handle 22 is tapered slightly at an angle $\theta_2$. The handle 22 has a length "l" and a thickness "t" (shown in FIG. 2) which is also the thickness of the midsection 18; the connecting section 20 and the working end 14.

The midsection 18 abuts the connecting section 20 and the working end 14 and generally has approximately the same width x as the connecting section 20, although in some embodiments, the midsection 18 and connecting section 20 are slightly tapered as will be explained below so that the width x varies along the longintudinal direction. Average typical values for the parameters defined above are as follows: L=3.877 inches; l=4.770 inches; w=0.400 inches; x=0.1335 inches; t=0.063 inches; θ=21.00 degrees; and $\theta_2$=1.30 degrees.

Figure 3:
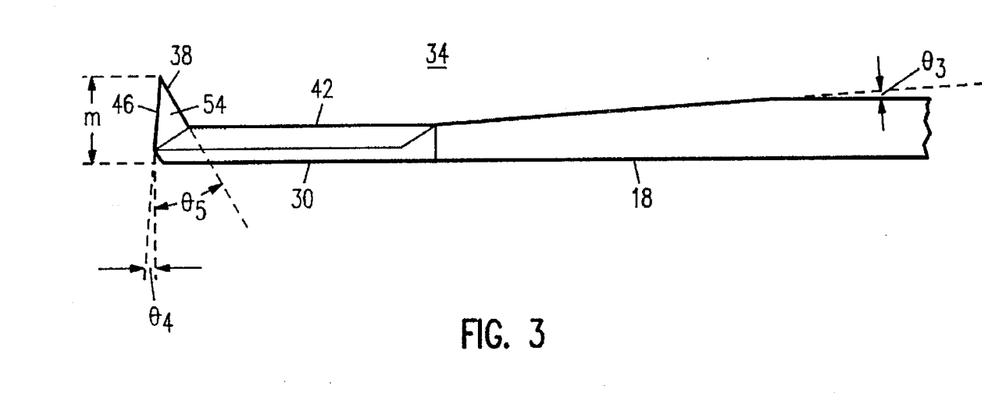
FIG. 3 is a partial side view of a puncture knife according to the present invention.

The working end 14 (shown in FIG. 1) designates the end of the angled surgical tool 10 that is modified to fulfill a specific surgical requirement such as puncturing a ligament, cuffing a ligament or cleaning away unwanted tissue. For example, FIG. 3 illustrates a puncture knife end 30 that is substituted for the working end 14 in the angled surgical tool 10 (shown in FIG. 1) to create a puncture knife 34. The puncture knife 34 includes the puncture knife end 30 (illustrated in FIG. 3) and the midsection 18, the connecting section 20 and the handle 22 (illustrated in FIG. 1) as described previously with respect to the angled surgical tool 10. In the puncture knife 34, part of the midsection 18 is angled slightly at an angle $\theta_3$.

The puncture knife end 30 is comprised of a pointed blade 38 and a longitudinal blade 42. The pointed blade 38 is comprised of a front face 46 and a two side faces 50 and 54 (more clearly shown in FIG. 4). The pointed blade 38 has a length "m" and the front face 46 is angled at the angle $\theta_4$ shown in FIG. 3. The side faces 50 and 54 are angled at the angle $\theta_5$ as shown in FIG. 3 and meet along an edge 56 (shown in FIG. 4) which is sharp and functions as a first knife edge capable of cutting tissue such as the transverse carpal ligament. Typically the faces 50 and 54 form a 34 degree angle where they meet along the edge 56.

Figure 4:
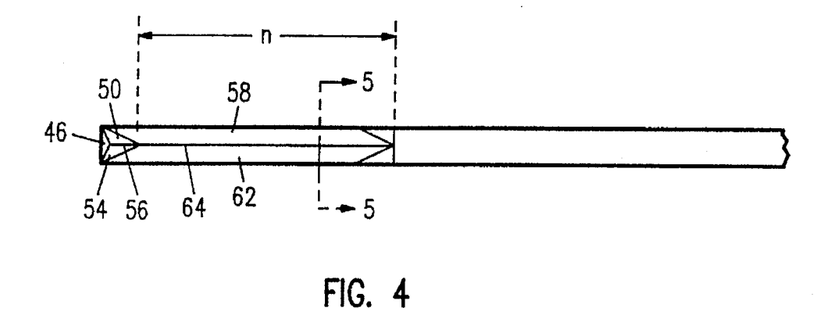
FIG. 4 is a top view of the puncture knife shown in FIG. 3.
Figure 5:
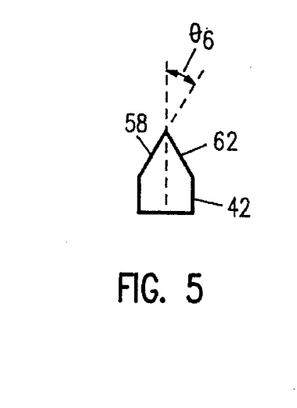
FIG. 5 is a cross-sectional view of the puncture knife taken along the line 5—5 shown in FIG. 4.

FIG. 4 illustrates that the longitudinal blade 42 is comprised of two angled faces 58 and 62 which meet along an edge 64 which is sharp and functions as a second knife edge capable of cutting tissue such as the transverse carpal ligament. The edge 64 has a length "n". The faces 58 and 62 are angled at the angle $\theta_6$ shown in FIG. 5. Average typical values for the parameters defined with respect to FIGS. 3–5 are as follows: m=0.165 inches; n=0.426 inches; $\theta_3$=6 degrees; $\theta_4$=5 degrees; $\theta_5$=30 degrees; and $\theta_6$=26.5 degrees.

Figure 6:
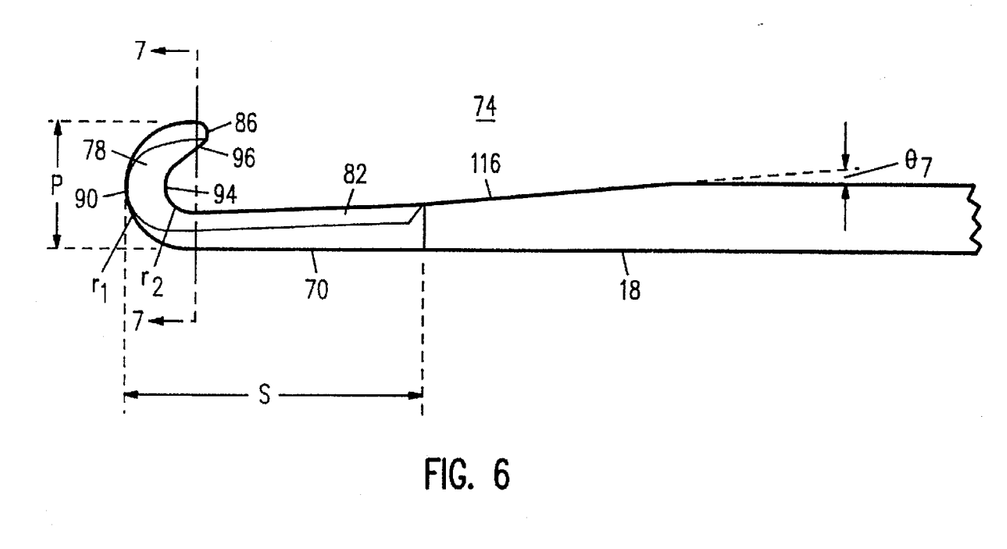
FIG. 6 is a side view of a reverse cut knife according to the present invention.

FIG. 6 illustrates a reverse cut knife end 70 that is substituted for the working end 14 in the angled surgical tool 10 (shown in FIG. 1) to create a reverse cut knife 74. The reverse cut knife 74 includes the reverse cut knife end 70 (illustrated in FIG. 6) and the midsection 18, the connecting section 20 and the handle 22 (illustrated in FIG. 1) as described previously with respect to the angled surgical tool 10. In the reverse cut knife 74, part of the midsection 18 is angled slightly at an angle $\theta_7$.

The reverse cut knife end 70 is comprised of a curved section 78 and a straight section 82. The reverse cut knife end 70 has a height "p" and a length "s". The curved section includes a blunt end 86 and a distal edge 90, neither of which are sharpened, and a proximal edge 94 that is sharpened. The distal edge 90 is a smooth curve defined by a radius $r_1$ (i.e. the curve comprises all the points contained in a segment formed by rotating a line of length $r_1$ about a fixed point). The distal edge 90 is not adapted for cutting tissue and is rounded to prevent such an occurrence. The proximal edge 94 includes a curved section defined by a radius $r_2$ and a straight section 96 that connects the curved section to the blunt end 86. The proximal edge 94 is a knife edge adapted for cutting tissue.

Figure 7:
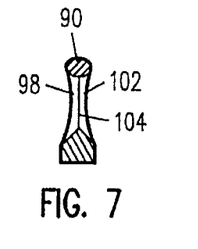
FIG. 7 is a cross-sectional view of the reverse cut knife taken along the line 7—7 shown in FIG. 6.

FIG. 7 illustrates that the proximal edge 94 comprises a pair of faces 98 and 102 that meet along an edge 104 that is sufficiently sharp to cut tissue such as the transverse carpal ligament (i.e. the edge 104 is a knife edge).

Figure 8:
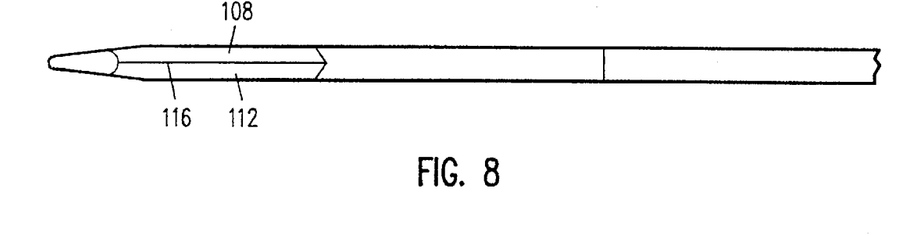
FIG. 8 is a top view of the reverse cut knife shown in FIG. 6.

FIG. 8 illustrates that the straight section 82 comprises a pair of faces 108 and 112 that meet along an edge 116 that is sufficiently sharp to cut tissue such as the transverse carpal ligament (i.e. the edge 116 is a knife edge). The faces 108 and 112 are positioned at angle to each other in the same manner as the faces 58 and 62 shown in FIG. 5. The straight section 82 extends approximately along a longitudinal axis of the midsection 18 (i.e. in the same direction as an upper edge 116 of the midsection 18) and is continuous with the curved section 78 meaning that the face 112 is continuous with the face 98 and the face 108 is continuous with the face 102.

Average typical values for the parameters defined with respect to FIGS. 6–7 are as follows: p=0.180 inches; s=0.500 inches; $r_1$=0.0865 inches; $r_2$=0.031 inches; $\theta_7$=3 degrees.

Figure 9:
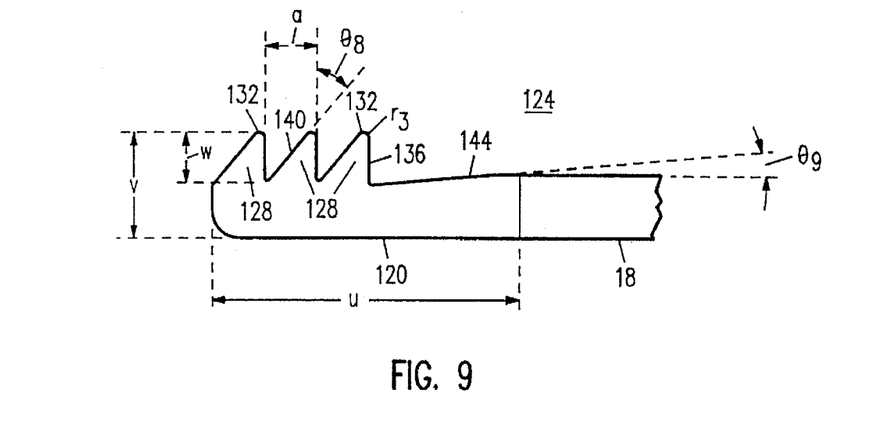
FIG. 9 is a partial side view of a rasp according to the present invention.

FIG. 9 illustrates a rasp end 120 that is substituted for the working end 14 in the angled surgical tool 10 (shown in FIG. 1) to create a rasp 124. The rasp 124 includes the rasp end 120 and the midsection 18, the connecting section 20 and the handle 22 (illustrated in FIG. 1) as described previously with respect to the angled surgical tool 10.

The rasp end 120 comprises three teeth 128 each having a top 132, a vertical side 136 and a sloped side 140. The tops 132 are rounded at a radius $r_3$. The rasp end 120 has a height "v" and the teeth 128 have a height "w". Adjacent vertical sides 136 are separated by a distance "a" and the rasp end 120 has a length "u". The sloped side 140 is positioned at an angle $\theta_8$ relative to the vertical side 136. A top edge 144 of the rasp end 120 is sloped at an angle $\theta_9$ between the teeth 128 and the midsection 18.

Average typical values for the parameters defined with respect to FIG. 9 are as follows: u=0.500 inches; v=0.165 inches; w=0.082 inches; a=0.095 inches; $r_3$=0.005 inches; $\theta_8$=40 degrees; and $\theta_9$=6 degrees.

Figure 10:
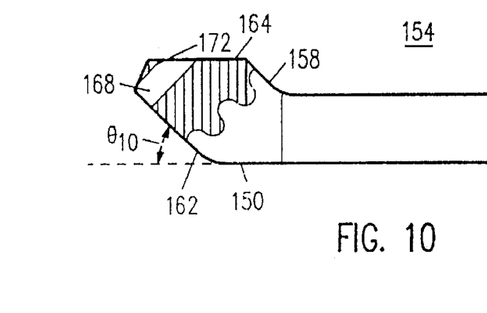
FIG. 10 is a partially sectioned, partial side view of a curette according to the present invention.

FIG. 10 illustrates a curette end 150 that is substituted for the working end 14 in the angled surgical tool 10 (shown in FIG. 1) to create a curette 154. The curette 154 includes the curette end 150 and the midsection 18, the connecting section 20 and the handle 22 (illustrated in FIG. 1) as described previously with respect to the angled surgical tool 10.

The curette end 150 comprises a scraping head 158 having a distal side 162 and a top side 164. An aperture 168 extends through the scraping head 158 and has a sharpened edge 172, which is capable of cutting tissue such as the ulnar bursa or the tenosynovium, positioned along part of the perimeter of the aperture 168 that interfaces with the top side 164. The distal side 162 is positioned at an angle $\theta_{10}$ relative to a bottom edge of the midsection 18. The top side 164 runs approximately parallel to a top side of the midsection 18.

Figure 11:
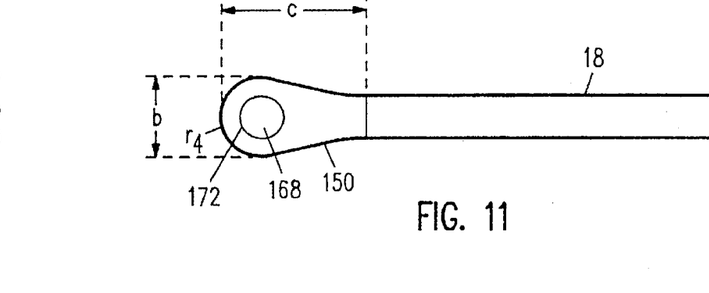
FIG. 11 is a top view of the curette shown in FIG. 10.

FIG. 11 is a top view of the curette end 150 showing that the scraping head 158 has a rounded edge 174 defined by a radius $r_4$ and a height "b". The curette end 150 has a length "c". Average typical values for the parameters defined with respect to FIGS. 10 and 11 are as follows: b=0.094 inches; c=0.147 inches; $r_4$=0.030 inches; and $\theta_{10}$=45 degrees.

Figure 12:
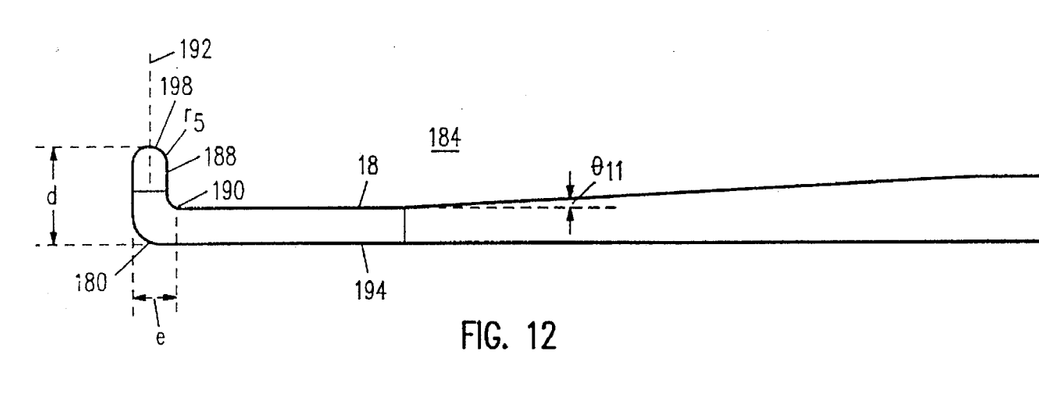
FIG. 12 is a partial side view of a probe according to the present invention.

FIG. 12 illustrates a probe end 180 that is substituted for the working end 14 in the angled surgical tool 10 (shown in FIG. 1) to create a right angle probe 184. The probe 184 includes the probe end 180 and the midsection 18, the connecting section 20 and the handle 22 (illustrated in FIG. 1) as described previously with respect to the angled surgical tool 10. In the probe 184, part of the midsection 18 is angled slightly at an angle $\theta_{11}$.

The probe end 180 is comprised of a cylindrical head 188 symmetrically positioned about an axis 192 that runs approximately perpendicular to the longitudinal direction of the midsection 18. In FIG. 12, a bottom edge 194 defines the longitudinal direction of the midsection 18. The cylindrical head 188 is connected to the midsection 18 by a bent section 190. In the preferred embodiment, the cylindrical head 188, the bent section 190 and the midsection 18 are all part of same piece of metal.

Figure 13:
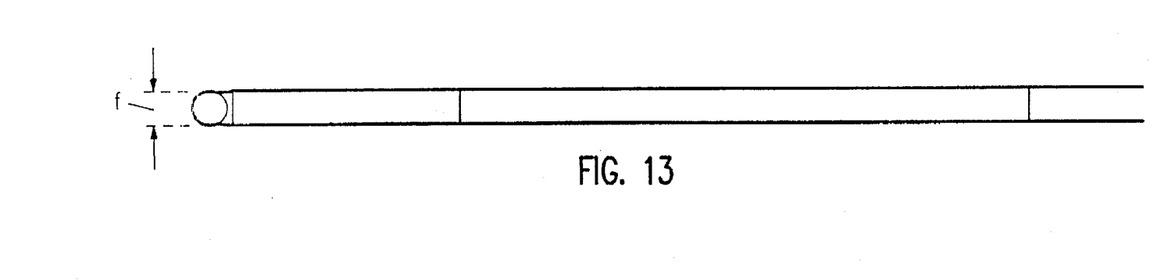
FIG. 13 is a top view of the probe shown in FIG. 12.

The cylindrical head 188 includes a top edge 198 that is rounded as defined by a radius $r_5$. The probe end 180 has a height "d" and a length "e". FIG. 13 illustrates that the probe end 180 has a width "f". Average typical values for the parameters defined with respect to FIGS. 12 and 13 are as follows: d=0.165 inches; e=0.060 inches; f=0.063 inches; $r_5$=0.03 inches; and $\theta_{11}$=3 degrees.

Figure 14:
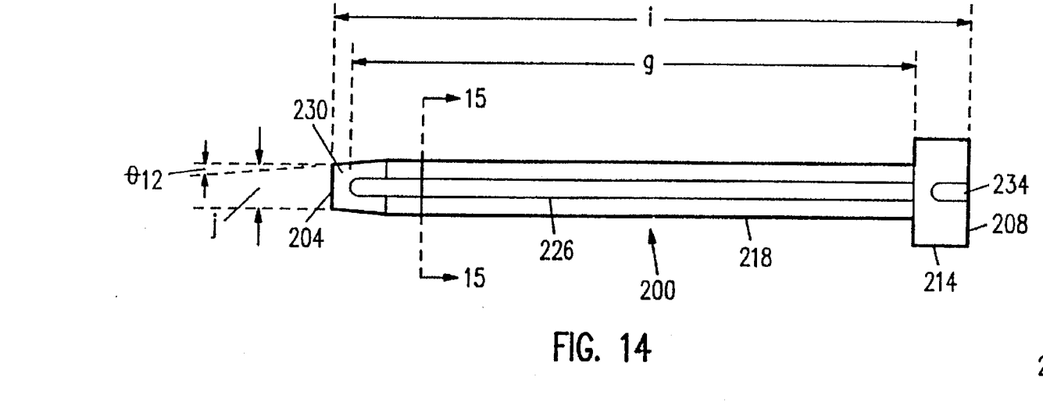
FIG. 14 is a side view of a slotted cannula according to the present invention.

FIG. 14 illustrates a slotted cannula 200 having a distal end 204 and a proximal end 208. A guard 214 is positioned at the proximal end 208 and a body 218 extends from the guard 214 to the distal end 204. A lumen 222 (shown in FIG. 15) extends through the body 218 and guard 214, thereby establishing a continuous passageway that extends from the proximal end 208 to the distal end 204. A slot 226, having a length "g", extends along the length of the body 218 from the guard 214 to a crosspiece 230. The slot 226 has a width "h" (shown in FIG. 15) that permits access to the lumen 222 along the length g. The lumen 222 has a diameter "x" (shown in FIG. 15). A notch 234 is located in the guard 214. As can be seen from FIG. 14, the notch 234 forms a marking means which is aligned with the slot 226. The slotted cannula 200 has a total length "i". The distal end 204 is tapered at the angle $\theta_{12}$ so that the crosspiece 230 has a diameter "j" that is slightly smaller than the diameter of the rest of the body 218.

Figure 14B:
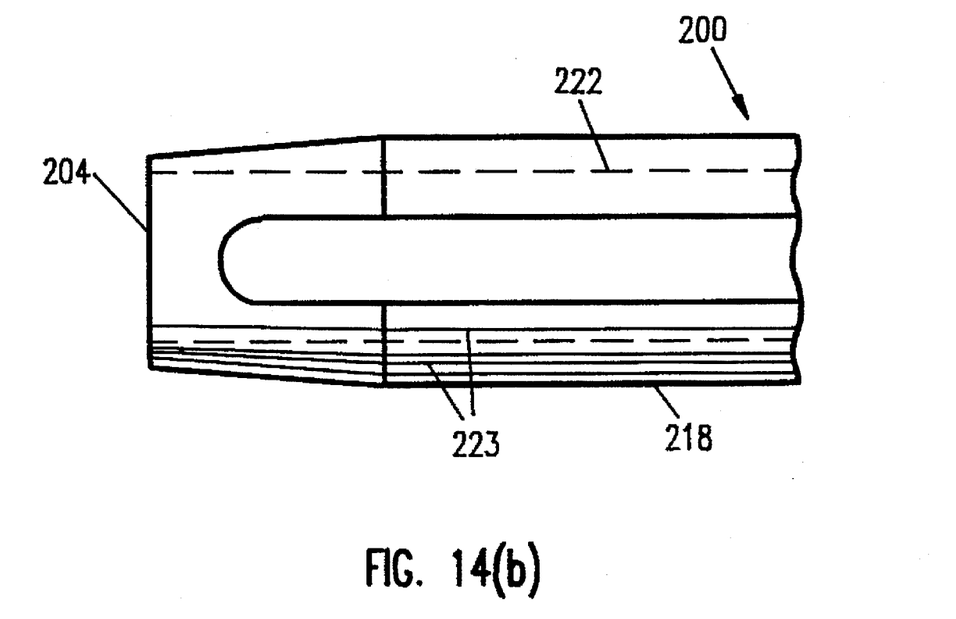
FIG. 14(b) is an enlarged view of the distal end of the cannula of FIG. 14 showing hidden detail by means of dashed lines.

FIG. 14(b) is an enlarged view of the distal end 204 of the slotted cannula 200. The lumen 222 is shown in hidden detail by means of dashed lines which illustrate how the lumen extends throught the body 218 and established a continuous passageway that extends from the distal end 204 as described above. Shading lines 223 illustrate the curvature of the outer surface of the slotted annula 200.

The slotted cannula 200 differs from slotted cannula of the prior art in that the slotted cannula 200 includes the crosspiece 230 and tapered angle $\theta_{12}$ which are not present in the cannula of the prior art. The crosspiece 230 prevents the body 218 from flaring out at the distal end 204. As used here, flaring out means having a diameter larger than the diameter of the rest of the body 218. The tapering at the distal end 230 of the slotted cannula 200 facilitates positioning of the cannula 200 during surgery.

Figure 16:
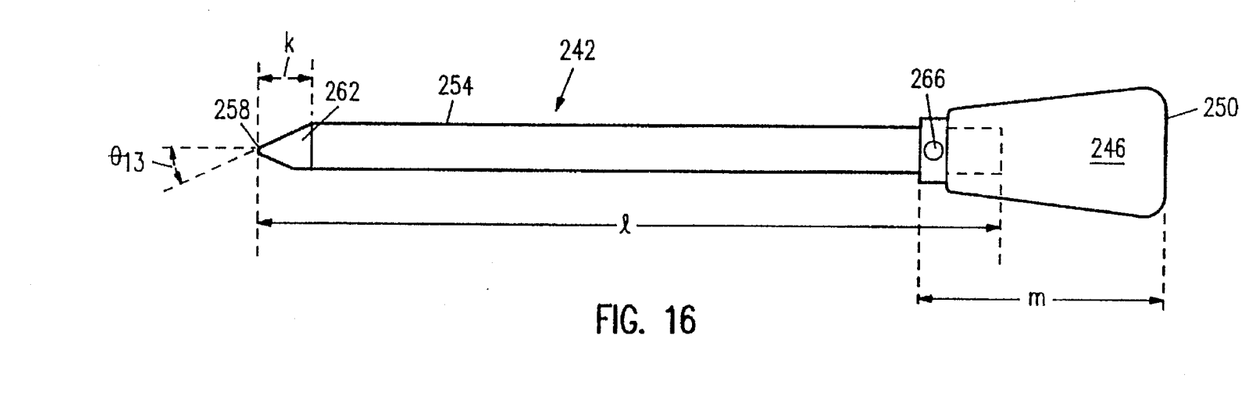
FIG. 16 is a side view of an obturator according to the present invention.

FIG. 16 illustrates an obturator 242 sized for insertion in the slotted cannula 200. The obturator 242 includes a handle 246 having a proximal end 250, and a stem 254 that extends from inside the handle 246 to a distal end 258. The stem 254 includes a section 262, having a length "k", positioned near the distal end 258 that is tapered at an angle $\theta_{13}$ to a rounded point. The stem 254 has a length "l" and the handle 246 has a length "m". The stem 254 and the handle 246 are separate pieces and a screw 266 provides a means for securing the stem 254 to the handle 246.

The obturator 242 is inserted in the cannula 200 (to form a cannula/obturator assembly) before the cannula is inserted into or removed from a surgical site inside the human body during surgery. This prevents tissue from getting caught in the slot 226 and also facilitates "steering" the cannula 200 so that it can be properly positioned.

Figure 15:
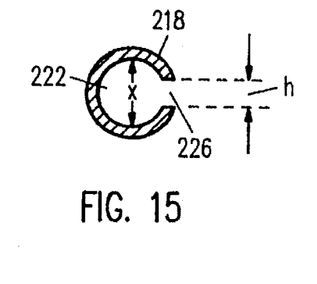
FIG. 15 is a cross-sectional view of the slotted cannula taken along the line 15—15 shown in FIG. 14.
Figure 17:
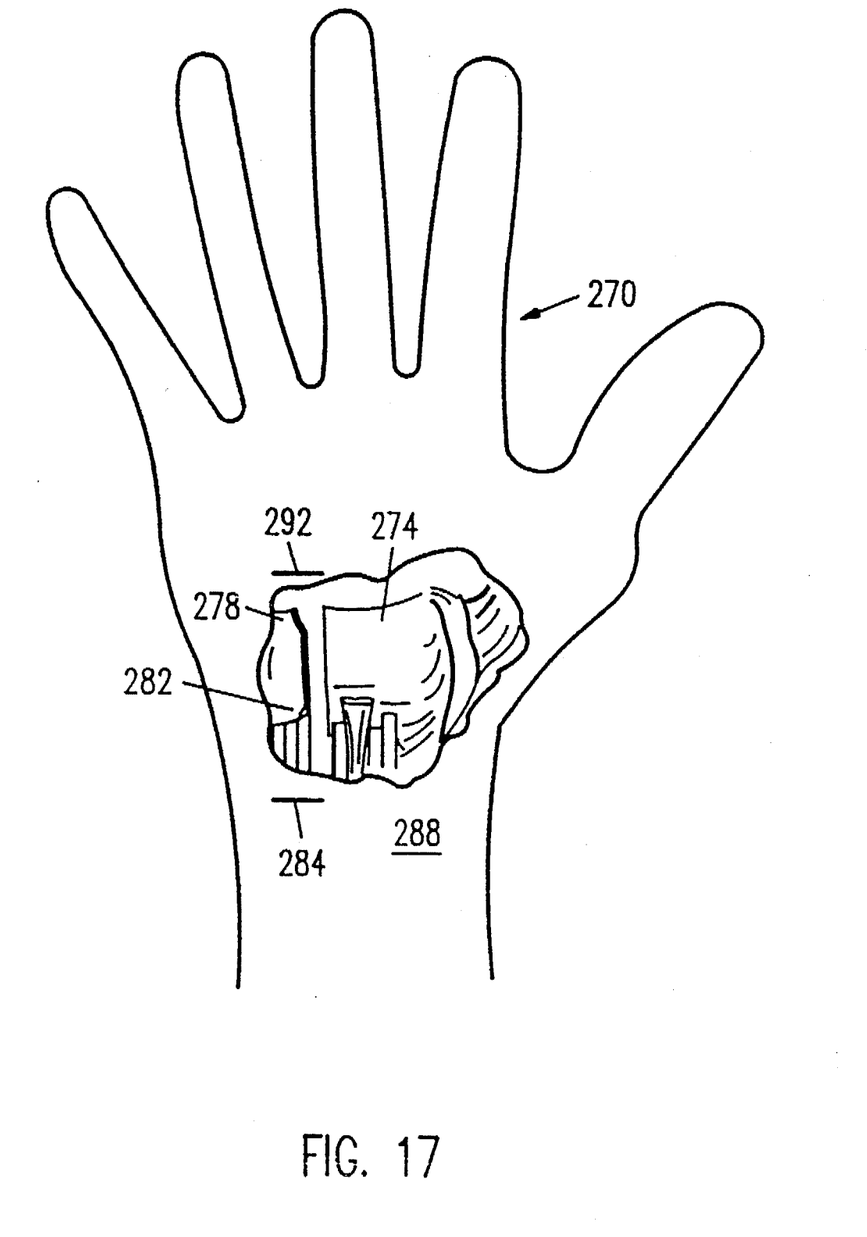
FIG. 17 illustrates the sectioned transverse carpal ligament in a human hand.

Average typical values for the parameters defined with respect to FIGS. 14–16 areas follows: h=0.110 inches; i=4.125 inches; j=0.213 inches; k=0.62 inches; l=6.22 inches; m=3.25 inches; x=0.189 inches; $\theta_{12}$=2 degrees; $\theta_{13}$=6 degrees;

FIG. 17 illustrates a human hand 270 with the cut-away portion showing a transverse carpal ligament 274 (shown in the completely released state), having a distal end 278 and a proximal end 282. An entry portal 284 is located near the proximal end 282 on a wrist area 288 and an exit portal 292 is located near the distal end 278 on the hand 270.

The method of the present invention for causing release of the transverse carpal ligament can now be explained. The surgical technique begins as any standard upper extremity procedure and is performed on an outpatient basis. The anesthesia can be either general, intravenous regional, or local, where local with standby or intravenous regional being the presently preferred method.

A tourniquet is placed on the proximal arm and the arm and hand are exsanguinated to create a bloodless field. On the volar aspect of the wrist 288, the pisiform is first palpated and then marked. The entrance portal 284 is found by measuring 1 cm radial to the radial border of the pisiform and then moving 1 cm proximal from this point, and 1 cm again from this point radially to the entrance portal 284 shown in FIG. 17, on the ulnar side of the palmaris longus tendon in line with the web between the middle and ring fingers. The portal 284 is made by incising only the skin at the last leg of this outline. The entrance portal 284 is approximately 1.0 cm in length and usually lies in the proximal volar wrist skin crease, just ulnar to the palmaris longus tendon.

The proximal and distal skin flaps are raised and the subcutaneous tissue is incised in the same fashion. Volar wrist veins are either retracted out of the way or coagulated using bipolar cautery, with retraction being the presently preferred method. The volar antebrachial fascia is incised in either a horizontal or longitudinal fashion, with the horizontal method being presently preferred, again staying on the ulnar side of the wrist flexor tendons.

The subligamentous approach of the present invention avoids the dissection to the floor of the flexor canal as described in the technique of Dr. Chow. Retractors are not used for either the flexor tendons or the ulnar nerve and artery. The volar fascia is simply opened and the tendons on the ulnar side of the carpal canal are visualized, but they are not retracted.

The slotted cannula 200/blunt obturator 242 assembly is placed under the flexor retinaculum using direct visualization. At this point, the skin retractors are removed from the entrance portal. An extension frame is placed under the dorsal side of the forearm and wrist, with the wrist gently extended over the frame. Gentle distally-directed pressure is placed on the cannula/obturator assembly, which is easily manipulated distally. The cannula/obturator assembly is "walked" under the transverse carpal ligament 274, in line with the ring finger metacarpal. The distal end 278 of the ligament can be palpated as the blunt obturator 242 exits underneath it. The tapered section 262 of the obturator 242 facilitates correct positioning of the cannula/obturator assembly.

The exit portal 292 in the palm of the hand 270 is identified by outlining Kaplan's Cardinal line. The exit portal 292 is located proximal to Kaplan's Cardinal line and is in line with the long-ring web. Identification of the exit portal 292 is extremely important because the superficial palmar vascular arch lies only 2–3 millimeters distal to this point (and Kaplan's Cardinal line).

The exit portal 292 is made by incising the skin only horizontally for a distance of approximately 4–5 millimeters over the palpable end of the blunt obturator 242, which is located superficially and is easily felt. The incision is made in the transverse direction, parallel to Kaplan's Cardinal line. Once the incision has been made, the blunt obturator 242/slotted cannula 200 assembly is pushed through the subcutaneous tissues and skin of the palm. The obturator 242 is removed from the cannula 200 and a standard 4.0 millimeter arthrosoope (now called an endoscope) is placed inside the cannula 200. Access to the transverse carpal ligament 274 is now available via the proximal end 208 and the distal end 204 of the cannula 200. Initially, the endoscope is placed in the proximal end 208 and the angled surgical tools 10 are placed in the distal end 204.

Visualization of the transverse carpal ligament 274 initially may be difficult at times due to edema within the ulnar bursa or the tenosynovium of the carpal canal. The edema may be removed using a sterile cotton-tipped swab inserted into the distal end 204. Visualization of the transverse carpal ligament 274 is through the slot 226 of the cannula 200. The tenosynovium that occasionally obscures the fibers of the transverse carpal ligament 274 must be removed. This is accomplished by inserting the rasp 124 (shown in FIG. 8) or the curette 154 (shown in FIGS. 9 and 10) into the cannula 200 through the distal end 204, and the ulnar bursa/tenosynovium is literally wiped or swept away under videoendoscopic control. Visualization of the transverse carpal ligament 274 is critical to ensure that none of the flexor tendons are trapped within the visualized space. If a flexor tendon is seen, it is usually the flexor digitorum superficialis to the little finger. If the flexor tendon cannot be removed from the visualized region of the transverse carpal ligament 274, it will be necessary to replace the blunt obturator 242 within the cannula 200, remove the assembled obturator and cannula from the flexor canal, and start the procedure over again, this time making sure that all of the flexor tendons are safely out of the way.

Once the transverse carpal ligament 274 is visualized, the release can be safely performed. The puncture knife 34 is inserted into the cannula 200 through the distal end 204 (the rasp 124 and/or curette 154 have been removed) and is used to create a hole in the distal end 278 of the transverse carpal ligament 274 (approximately in the distal third of the ligament 274). The puncture knife 34 is removed from the cannula 200 and the reverse cut knife 74 is inserted into the cannula 200 through the distal end 204. The hole in the transverse carpal ligament 274 is then enlarged by cutting the ligament 274 in a proximal to distal direction with the knife 74 (i.e. by using the knife 74 in a retrograde fashion).

The entire transection of the transverse carpal ligament 274 is done under direct visualization with the videoendoscope, using standard arthroscopic techniques. With the observance of the herniation of palmar adipose tissue or with the visualization of the palmaris brevis muscle, the release of the ligament is completed for that area. After the distal portion of the transverse carpal ligament has been released, the endoscope is removed from the entry port 222 of the cannula 200 and the knife 74 is removed from the distal end 204 of the cannula 200. The endoscope is then inserted into the distal end 204 of the cannula 200. The distal extent of the ligament release is established. It may be necessary to use cotton-tipped swabs to remove excess edema or loose particles of tissue. The reverse cut knife 74 is then inserted into the cannula 200 through the proximal end 208 and the proximal half of the transverse carpal ligament is released or cut, again under direct videoendoscopic control and again using the knife 74 in a retrograde manner to cut the ligament 274 from the distal to the proximal direction. When the palmaris brevis muscle is seen or the palmar adipose tissue herniams through the transected ligament, the release is completed. Small retained bands of the ligament that may remain intact are released using either the knife 74 or the probe 180 (shown in FIGS. 11 and 12). Care is taken not to cut the skin as the knife is brought close to the portal areas 284 and 292.

After the ligament 274 has been released, the endoscope and any of the angled surgical tools 10 remaining in the cannula 200 are removed from the cannula 200. The obturator 242 is then placed back in the cannula 200 and the obturator/cannula assembly is removed from the flexor canal. The tourniquet is deflated and the skin portal sites are irrigated with an antiseptic solution. The portal sites 284 and 292 are closed with one or two throws of 4-0 or 5-0 nonabsorbable monofilament suture. The portal sites are covered with antiseptic material, and a small figure-of-eight dressing is placed on the hand and wrist. Splints and/or cast are not applied. The natural flexion posture of the digits of the hand and the flexion/extension tenedesis effects of the fingers are observed at the immediate postoperative physical examination to assure that no iatrogenic flexor tendon laceration has occurred.

In the recovery room, once the anesthesia has resolved, a postoperative physical examination is performed to assess the integrity of the median and ulnar nerves as well as the flexor tendons. Each of the flexor digitorum superficialis and profundus tendons is examined. The intrinsic muscles are examined. The patient is asked to abduct and to adduct the fingers against resistance, and the resting posture of the flexed fingers is observed. Lastly, the sensory and motor patterns of the median and ulnar nerves are tested and documented to assure that no violation has occurred.

In the method of the present invention, when the angled surgical tools 10 such as the puncture knife 34 or the reverse cut knife 74 are inserted into the cannula 200, they are inserted with the cutting blades rotated approximately 90 degrees to the slot 226 of the cannula 200. This reduces the likelihood that tissue along the slot 226 will be accidentally cut. When the tool 10 is in position, it is then rotated back into a cutting position. This procedure implies that the width x of the lumen 222 (shown in FIG. 15) is large enough to accommodate rotation of the tools 10.

The present invention has been particularly shown and described with respect to certain preferred embodiments of features thereof. However, it should be readily apparent to those of ordinary skill in the art that various changes and modifications in form and details may be made without departing from the spirit and scope of the invention as set forth in the appended claims.

We claim:

1. An instrument for use in endoscopic surgical procedures, the procedures including use of an endoscope and a surgical instrument, the instrument comprising:

a cannula having proximal and distal open ends, the cannula defining a continuous passageway that extends through the cannula from the proximal end to the distal end, the cannula having a slot defined along substantially all of its length through which tissue can be viewed and accessed, the slot being bounded by a crosspiece at the distal end.

2. The cannula of claim 1 wherein the circumference of the body of the cannula is inwardly tapered toward the longitudinal axis thereof at the distal end.

3. The cannula of claim 1 wherein the slot is bounded by a guard at the proximal end.

4. The cannula of claim 3 wherein the guard includes marking means, aligned with the slot for indicating orientation thereof with respect to said tissue.

* * * * *